US00PP30697P3

(12) United States Plant Patent
Kuehne

(10) Patent No.: US PP30,697 P3
(45) Date of Patent: Jul. 9, 2019

(54) ***LOBELIA* PLANT NAMED 'LOCPI03-0'**

(50) Latin Name: *Lobelia erinus*
Varietal Denomination: LOCPI03-0

(71) Applicant: Torsten Kuehne, Dresden (DE)

(72) Inventor: Torsten Kuehne, Dresden (DE)

(73) Assignee: Kuehne Jungpflanzen (DE)

( * ) Notice: Subject to any disclaimer, the term of this patent is extended or adjusted under 35 U.S.C. 154(b) by 0 days.

(21) Appl. No.: 15/732,340

(22) Filed: Oct. 25, 2017

(65) Prior Publication Data

US 2019/0124816 P1 Apr. 25, 2019

(51) Int. Cl.
*A01H 5/02* (2018.01)
*A01H 6/26* (2018.01)

(52) U.S. Cl.
USPC ..... Plt./451
CPC ..... *A01H 6/268* (2018.05)

(58) Field of Classification Search
USPC ..... Plt./263.1, 451
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Lobelia erinus* cultivar named 'LOCPI03-0' is disclosed, characterized by very well-branched, compact plants. Flowers are large and distinctively light purple with a white throat infrequently striped dark purple. The new variety is a *Lobelia*, and is normally used as an ornamental garden or container plant.

2 Drawing Sheets

Figure 1:
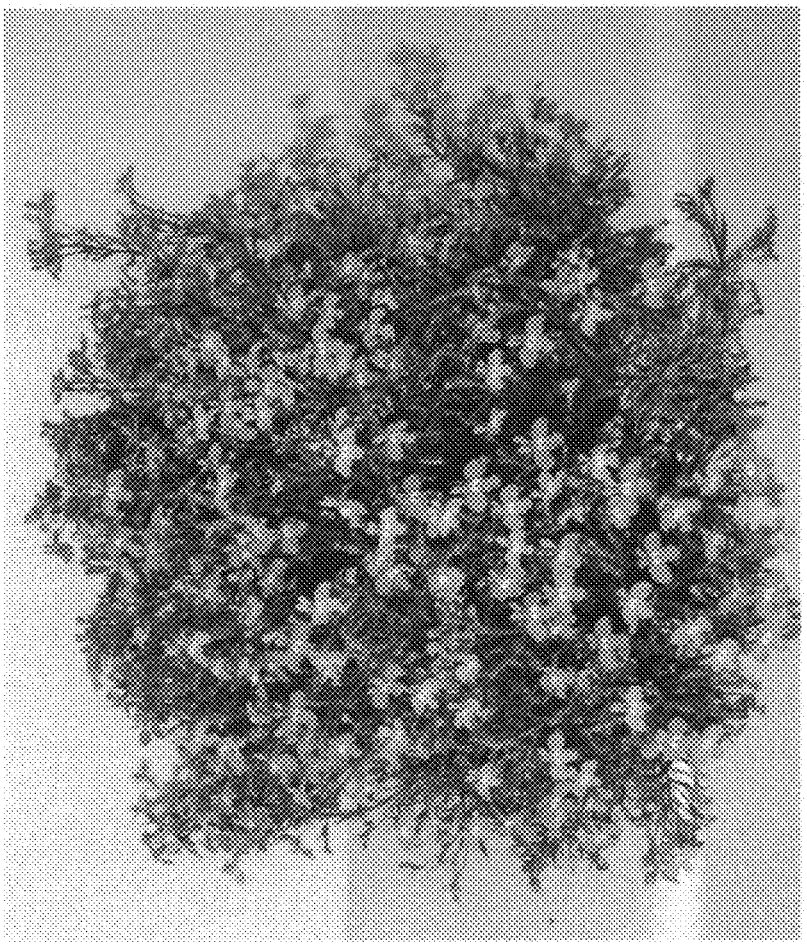

Latin name of the genus and species: *Lobelia erinus*.
Variety denomination: 'LOCPI03-0'.

BACKGROUND OF THE INVENTION

The new cultivar is the product of a breeding program, with the object to develop floriferous compact *Lobelia* varieties for commercial applications. The new variety originated from a crossing of the seed parent, an unnamed proprietary *Lobelia erinus* with the pollen parent, also an unnamed, unpatented proprietary *Lobelia erinus*. The cross resulting in the new variety was made June 2013 at a research greenhouse in Dresden, Germany.

The new variety was selected by the inventor, during June of 2014 at a research nursery in greenhouse in Dresden, Germany. After identifying the new variety as a potentially interesting selection, the inventor continued confidential testing and propagation of 'LOCPI03-0' assessing stability of the unique characteristics of this variety.

Asexual reproduction of the new cultivar 'LOCPI03-0' was first performed in Dresden, Germany by vegetative terminal cuttings in August of 2014. 'LOCPI03-0' has since been reproduced over multiple generations and has shown that the unique features of this cultivar are stable and reproduced true to type.

SUMMARY OF THE INVENTION

The cultivar 'LOCPI03-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOCPI03-0'. These characteristics in combination distinguish 'LOCPI03-0' as a new and distinct *Lobelia erinus* cultivar:

1. Large flowers.
2. Compact plant habit.
3. Light purple flowers with a white throat having infrequent dark purple stripes.
4. Improved branching, producing more branches per plant than typically observed in commercial varieties.

PARENT COMPARISON

Plants of the new cultivar 'LOCPI03-0' are similar to the seed parent in most horticultural characteristics. The new variety, however, differs in the following:

1. The new variety produces pink flowers compared to the blue flower of the seed parent Plants of the new cultivar 'LOCPI03-0' are similar to the pollen parent in most horticultural characteristics. The new variety, however, differs in the following:

1. The new variety produces pink flowers compared to the blue flower of the pollen parent.

COMMERCIAL COMPARISON

Plants of the new cultivar 'LOCPI03-0' are similar to plants of the commercial variety, *Lobelia erinus* 'Africo Lavender', unpatented, in most horticultural characteristics. However, plants of the new cultivar 'LOCPI03-0' differ in the following:

1. Plants of the new variety are more compact than this comparator.
2. Plants of the new variety produce a brighter colored flower than plants of this comparator.

Plants of the new cultivar 'LOCPI03-0' are similar to plants of the commercial variety, *Lobelia erinus*

'Weslodala', unpatented, in most horticultural characteristics. However, plants of the new cultivar 'LOCPI03-0' differ in the following:

1. Plants of the new variety produce larger flowers than this comparator.
2. Plants of the new variety produce more branches than plants of this comparator.

BRIEF DESCRIPTION OF THE PHOTOGRAPHS

The accompanying photograph in FIG. 1 illustrates in full color a typical plant of 'LOCPI03-0' grown in a greenhouse and photographed in June, after a month of high temperatures. The pot size is a commercial 10 inch pot. The plant shown is approximately 20 weeks old.

Figure 2:
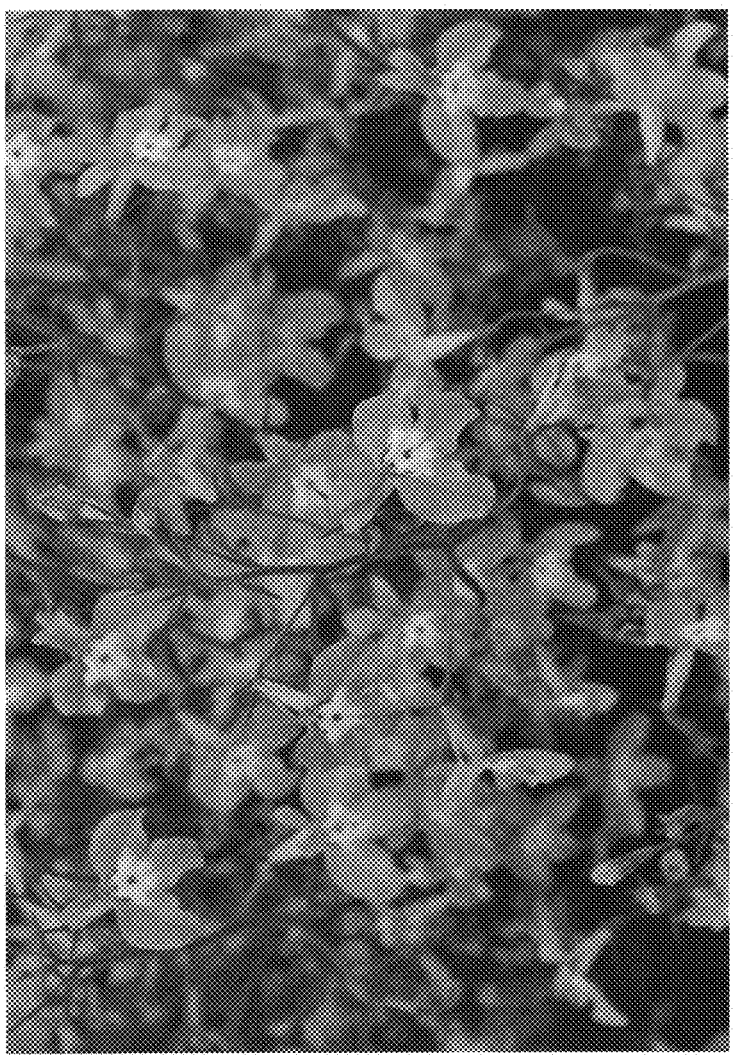

FIG. 2 illustrates a close up of flowers of the new variety, photographed during April under slightly cooler conditions than the plant in FIG. 1.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LOCPI03-0' plants grown in a commercial controlled greenhouse in Santa Paula, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.

Botanical classification: *Lobelia erinus* 'LOCPI03-0'.

PROPAGATION

Time to initiate roots: About 8 to 14 days at approximately 25° C.

Root description: Fibrous, colored near RHS Greyed-Orange 165D.

PLANT

Growth habit: Mounded flowering annual.

Height: 13 cm.

Plant spread: 45 cm.

Growth rate: Moderate to rapid.

Branching characteristics: Very well branched, having improved branching, producing more branches per plant than typically observed in commercial varieties.

Length of primary lateral branches: Average range 12 to 20 cm.

Diameter of lateral branches: 3 mm.

Quantity of primary lateral branches: About 200.

Characteristics of primary lateral branches:

*Form*.—Round.

*Color*.—Near RHS Green 138B, flushed greyed-Purple N186C and N187B.

*Texture*.—Soft, short, dense pubescence.

*Strength*.—Moderately flexible and strong.

Internode length: Average range 1.0 to 2.5 cm.

FOLIAGE

Leaf:

*Arrangement*.—Alternate.

*Quantity*.—Approximately 10 to 20 per branch.

*Average length*.—1.5 to 2.5 cm.

*Average width*.—4 to 6 mm.

*Shape of blade*.—Lanceolate to narrow elliptic.

*Apex*.—Acute.

*Base*.—Truncate.

*Margin*.—Sparse dentations.

*Texture of top surface*.—Softly pubescent.

*Texture of bottom surface*.—Softly pubescent.

*Aspect*.—Slightly to moderately folded upward from mid-vein.

*Color*.—Young foliage upper side: RHS Green 137B. Young foliage under side: RHS Green 138B. Mature foliage upper side: RHS Green 139A, lightly flushed N187A at apex. Mature foliage under side: RHS Green 139A, heavily covered in N186C.

*Venation*.—Type: Pinnate. Venation color upper side: RHS Green 137C. Venation color under side: RHS Green 139A.

*Petiole*.—Sessile.

FLOWER

Natural flowering season: Flowering occurs continuously during growing season from spring until fall under Southern California climatic conditions. Flowering begins approximately 3 weeks after planting a rooted cutting.

Flower type and habit: Flowers arranged singly at lateral apices.

Number of flowers per plant: Approximately 500.

Fragrance: None

Longevity: Depending on weather conditions, 7-14 days for single flower. Flowering season for the entire plant lasts approximately 250 days.

Flower size:

*Overall length*.—1.7 cm.

*Overall width*.—2.3 cm.

*Tube length*.—1 cm.

*Diameter*.—Distal end: 4 mm. Proximal end: 2 mm.

Flower shape and petal arrangement: Tubular with three larger lower petals and two upright petals.

Bud:

*Shape*.—Conical with a distal sphere.

*Length*.—1.3 cm.

*Diameter*.—5 mm.

*Color*.—Near RHS White 155A, distal sphere flushed Purple 77D.

Corolla:

*Petals/lobes*.—Number: 5 total, 3 large lower and 2 smaller upper petals. Upper petals. Length: 1.2 cm. Width: 0.7 cm. Lower petals. Length: 1.0 cm. Width: 0.6 cm. Shape: Obovate. Aspect: Slightly undulate. Margin: Entire, moderately undulate. Texture: Smooth. Color: When opening: Upper surface: Near RHS Purple 76A. Lower surface: Near RHS Purple 76B, blotched Purple 77A, base White N155B. Fully opened: Upper surface: Near RHS Purple 76A, margins 76B. Lower surface: Near RHS Violet-Purple N80D, mid vein N79C, base White N155B. Throat: Color: Near RHS White N155D, striped Purple N79B, white section may have a very small flush Yellow 9B. Texture: Glabrous. Tube color: Interior: Near RHS White N155B, striped N79B. Exterior: Near RHS Violet-Purple N80C, base White N155B.

Calyx:

*Form*.—Star-shaped structure composed of 5 sepals fused at base.

*Length*.—1.4 cm.

*Diameter*.—1.5 cm.

*Sepal shape*.—Lanceolate.

*Sepal margin*.—Entire.

*Sepal texture*.—Softly pubescent all surfaces.

*Sepal color*.—Upper surface: Near Green 137A flushed N187A. Lower surface: Near Green 137A flushed N187A.

Fragrance: None.

Peduncles:

*Length*.—About 2.0 cm.

*Diameter*.—About 0.8 mm.

*Color*.—147B, flushed N187A.

*Texture*.—Dense, soft pubescence.

*Aspect*.—Straight.

*Strength*.—Wiry, flexible.

REPRODUCTIVE ORGANS

Stamens:

*Number*.—8.

*Filament length*.—Approximately 1.5 cm.

Anthers:

*Shape*.—Linear.

*Length*.—Approximately 0.5 cm.

*Color*.—Near RHS Greyed-Yellow 161B.

*Pollen*.—Color: Near RHS Greyed-Yellow 161D. Quantity: Scant.

Pistil:

*Number*.—1.

*Length*.—3.0 cm.

*Style*.—Length: 1.8 cm. Color: Near RHS White N155D.

*Stigma*.—Shape: Bi lobed. Color: Near RHS Green-White 157A.

*Ovary*.—Ovary Color: Near RHS Yellow-Green 145A. Ovary Length: Approximately 1.2 cm. Ovary diameter: Approximately 0.1 cm. Ovary shape: Linear.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately −5° to 35-8° C.

What is claimed is:

1. A new and distinct cultivar of *Lobelia* plant named 'LOCPI03-0' as herein illustrated and described.

* * * * *